United States Patent [19]
Freiberg

[11] 3,932,383
[45] Jan. 13, 1976

[54] 9-DIHYDRONIDDAMYCIN A COMPOUNDS AND RELATED 3-(O)-ESTERS AND THE PROCESS FOR THEIR PREPARATION

[75] Inventor: Leslie Alan Freiberg, Waukegan, Ill.

[73] Assignee: Abbott Laboratories, North Chicago, Ill.

[22] Filed: June 3, 1974

[21] Appl. No.: 476,015

[52] U.S. Cl............................ 260/210 AB; 424/180
[51] Int. Cl.² ......................................... C07G 3/00
[58] Field of Search....... 260/210 AB, 210 E, 210 K

[56] References Cited
UNITED STATES PATENTS

| | | | |
|---|---|---|---|
| 3,784,447 | 1/1974 | Theriault...................... | 260/210 AB |
| 3,792,035 | 2/1974 | Fukatsu et al................ | 260/210 AB |

OTHER PUBLICATIONS

Wagner & Zook, Syn. Org. Chemistry, pp. 261 and 293, Wiley & Sons, Inc., New York, 1953.
Gaylord, Reduction W/Complex Metal Hydrides, p. 308, Interscience Publisher's Ltd., New York, 1956.

*Primary Examiner*—Lewis Gotts
*Assistant Examiner*—Cary Owens
*Attorney, Agent, or Firm*—Robert L. Niblack; Vincent A. Mallare

[57] ABSTRACT

Covers 9-dihydroniddamycin A compounds and related 3-(O)-esters, which are active antimicrobial agents, and the process for their preparation. These compounds are represented by the general formula:

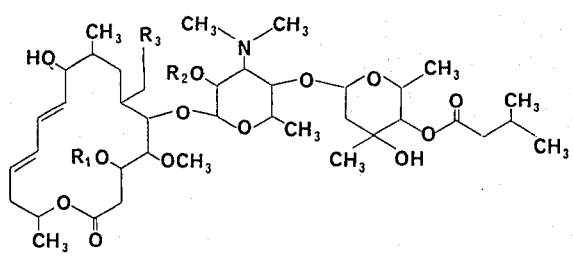

wherein $R_1$ is hydrogen, HCO (formyl), $CH_3CO$ (acetyl), $C_2H_5CO$ (propionyl) or $C_3H_7CO$ (butyryl); $R_2$ is hydrogen or equal to $R_1$ and $R_3$ is CHO or $CH(OCH_3)_2$.

24 Claims, No Drawings

9-DIHYDRONIDDAMYCIN A COMPOUNDS AND RELATED 3-(O)-ESTERS AND THE PROCESS FOR THEIR PREPARATION

DISCLOSURE OF THE INVENTION

This invention relates to dihydroniddamycin compounds. More particularly, it relates to 9-dihydroniddamycin A compounds and related 3-(O)-esters that are active in inhibiting microorganism growth such as *Staphylococcus aureus* Wise 155, *Mycoplasma gallispeticum* S6, and *Haemophilus influenzae*. The compounds of the present invention have the general structural formula:

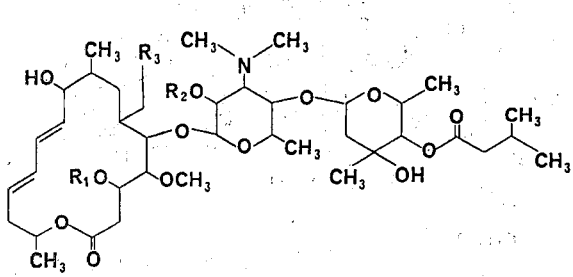

wherein $R_1$ is hydrogen, HCO (formyl), $CH_3CO$ (acetyl), $C_2H_5CO$ (propionyl) or $C_3H_7CO$ (butyryl); $R_2$ is hydrogen or equal to $R_1$ and $R_3$ is CHO or $CH(OCH_3)_2$. The present compounds have a high antimicrobial activity.

The compounds of the invention are prepared as shown in the synthesis flow chart below, from niddamycin (1) which is first converted to niddamycin dimethyl acetal (2) by reaction with methanol in the presence of a carefully measured amount of a strong acid catalyst such as hydrochloric acid. The acid catalyst may also be a weak acid such as p-nitrobenzoic, chloroacetic or difluoroacetic acid added in sufficient quantity to achieve a suitable reaction rate. The reaction can be carried out at temperatures between 0° and 64° C. for times varying between a few hours to several weeks depending on the choice of acid catalyst, its concentration and the temperature of the reaction. This process minimizes acid catalyzed removal of the neutral sugar observed with strong acid solutions, as shown in [Omura, et al., *Chem. Pharm. Bull.* (Tokyo), 16, 1167 (1968)]. The intermediate niddamycin dimethyl acetal (2) is reduced with lithium borohydride ($LiBH_4$) in dioxane which provides a mixture of epimers, 9-dihydroniddamycins A and B, from which the predominant product, 9-dihydroniddamycin A dimethyl acetal (3), is isolated by chromatography. The dimethyl acetal (3) yields the desired product, 9-dihydroniddamycin A (5), by hydrolysis with difluoroacetic acid ($CHF_2CO_2H$) in $CH_3CN$-$H_2O$. This product (9-dihydroniddamycin A) is shown to be different from leucomycin $A_1$ (9-dihydroniddamycin B) by its mobility on thin-layer-chromatographic plates.

In the synthesis of 3-(O)-acetyl-9-dihydroniddamycin A, where $R_1$ is acetyl, the intermediate niddamycin dimethyl acetal (2) is acetylated with acetic anhydride-pyridine, to provide 2',3-di-(O)-acetylniddamycin dimethyl acetal (4B). In the acetylation of the intermediate niddamycin dimethyl acetal (2) other anhydrides may be used to provide 2',3-di-(O)-acylniddamycin dimethyl acetal (4). The other anhydrides that may be used include propionic anhydride ($R_1=R_2=C_2H_5CO$), butyric anhydride ($R_1=R_2=C_3H_7CO$), or a mixed anhydride such as formic acetic anhydride

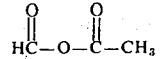

(when $R_1=R_2=HCO$. This material, 2',3-di-(O)-acetylniddamycin dimethyl acetal (4B) (when $R_1=R_2=CH_3CO$), on hydrolysis with sodium bicarbonate ($NaHCO_3$) in an aqueous solution of methyl alcohol ($CH_3OH$—$H_2O$) yields 3-(O)-acetylniddamycin dimethyl acetal (6B). In the hydrolysis of 2',3-di-(O)-acylniddamycin dimethyl acetal (4), products other than the 3-(O)-acetylniddamycin dimethyl acetal (6B) may be obtained depending on the value of $R_1$ and $R_2$. The product when $R_1=R_2=HCO$ is 3-(O)-formylniddamycin dimethyl acetal (6A); when $R_1=R_2=C_2H_5CO$, the product is 3-(O)-propionylniddamycin dimethyl acetal (6C); and when $R_1=R_2=C_3H_7CO$, the product is 3-(O)-butyrylniddamycin dimethyl acetal (6D). In this hydrolysis process, the 2'-acyl group, e.g. the 2'-acetate group, being vicinal to the dimethylamino group is activated and hydrolyzed under mild basic conditions which do not hydrolyze an unactivated acyl group such as that at the 3-position. The hydrolysis is carried out at 0° to 50° C. in the presence of a slight excess of bicarbonate in a mixture of an aqueous organic solvent. Although methanol is preferable as an organic solvent, other water-soluble solvents such as acetonitrile or ethanol may be used.

After being hydrolyzed, the 3-(O)-acetylniddamycin dimethyl acetal (6B) is then reduced with lithium borohydride in an aprotic solvent such as dioxane which reduction is of the 9-keto group and provides a mixture of epimers, 3-(O)-acetyl-9-dihydroniddamycins A and B, from which the major product, 3-(O)-acetyl-9-dihydroniddamycin A dimethyl acetal (7B), is isolated by chromatography.

In the reduction of 3-(O)-acetylniddamycin dimethyl acetal (6B) with lithium borohydride in dioxane, the reduced product, i.e. 3-(O)-acetyl-9-dihydroniddamycin A dimethyl acetal (7B), corresponds to the value of $R_1$ which is $CH_3CO$. Accordingly, the product (7), when $R_1$ is HCO, is 3-(O)-formyl-9-dihydroniddamycin A dimethyl acetal (7A); when $R_1$ is $C_2H_5CO$, the product is 3-(O)-propionyl-9-dihydroniddamycin A dimethyl acetal (7C); and when $R_1$ is $C_3H_7CO$, the product is 3-(O)-butyryl-9-dihydroniddamycin A dimethyl acetal (7D). The reaction temperatures during the reduction range from 0° to 50° C. and the reduction is completed in 1 to 24 hours. Other solvents may be used such as ethyl acetate or other reducing agents may be used such as sodium borohydride or sodium trimethylborohydride [$NaBH(OCH_3)_3$].

The desired product (8B), 3-(O)-acetyl-9-dihydroniddamycin A, which is different from leucomycin $A_3$ on thinlayer chromatography is provided by the hydrolysis of the dimethyl acetal (7B) in a mixed solvent of 50% acetonitrile-water ($CH_3CN$-$H_2O$) in the presence of about 2.5 equivalents of difluoroacetic acid as an acid catalyst. The organic solvent is not necessary for the reaction as the acid salt of the macrolide is sufficiently soluble in water. However, if the acetonitrile is not used, the amount of weak acid used must be less since the degree of ionization will increase, thereby increasing the proton concentration and the reaction rate. Conversely, if less water is used more of the acid catalyst must be used to maintain the same reaction rate. Depending on the exact conditions, the reaction is complete in 2 to 20 hours at temperatures ranging from 0° to 50° C.

As with the product (7), the desired product (8), i.e., 3-(O)-acyl-9-dihydroniddamycin A, will vary as to the corresponding value of $R_1$ which is $CH_3CO$ for product (8B). Accordingly, when $R_1$ is HCO, the product is 3-(O)-formyl-9-dihydroniddamycin A (8A); when $R_1$ is $C_2H_5CO$, the product is 3-(O)-propionyl-9-dihydroniddamycin A (8C); and when $R_1$ is $C_3H_7CO$, the product is 3-(O)-butyryl-9-dihydroniddamycin A (8D).

The synthesis of the compounds of this invention are provided in the flow charts below, which have numerals to correspond with the structural compounds set forth above.

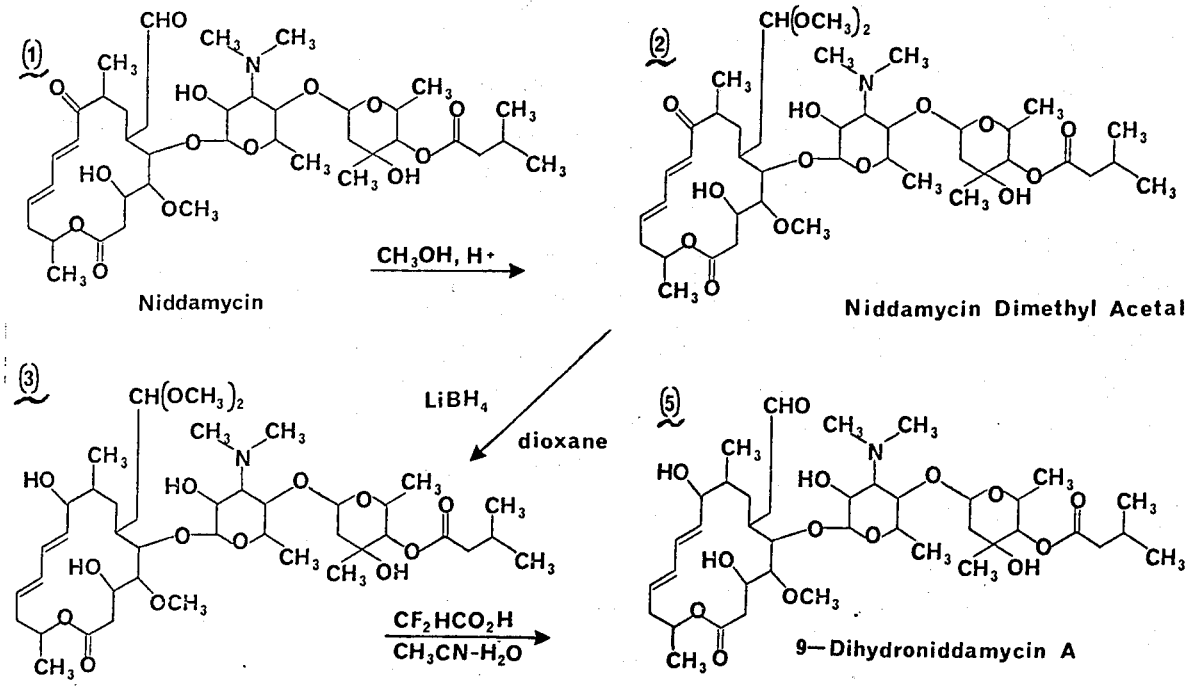

Flow Chart for Synthesis of 9-Dihydroniddamycin A

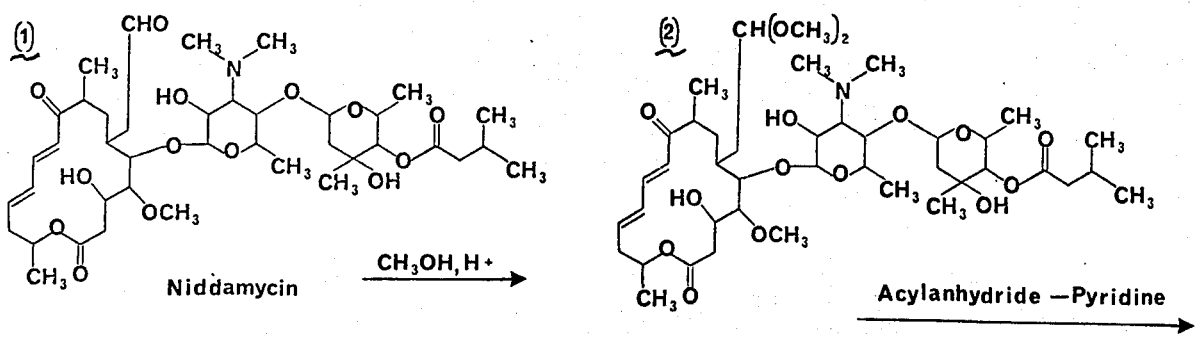

Flow Chart for Synthesis of 3-(O)-Acetyl-9-Dihydroniddamycin A And Related 3-(O)-Esters Flow Chart for Synthesis of 3-(O)-Acetyl-9-Dihydroniddamycin A
And Related 3-(O)-Esters (Cont'd.)

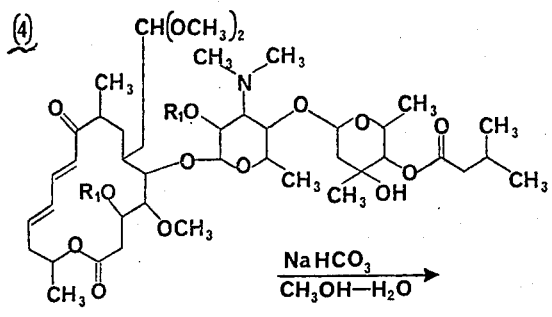

(4A) R₁ = HCO
(4B) R₁ = CH₃CO
(4C) R₁ = C₂H₅CO
(4D) R₁ = C₃H₇CO

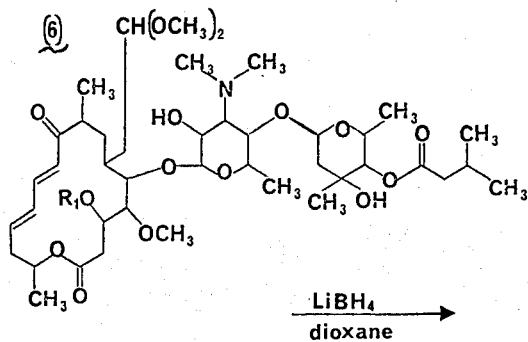

(6A) R₁ = HCO
(6B) R₁ = CH₃CO
(6C) R₁ = C₂H₅CO
(6D) R₁ = C₃H₇CO

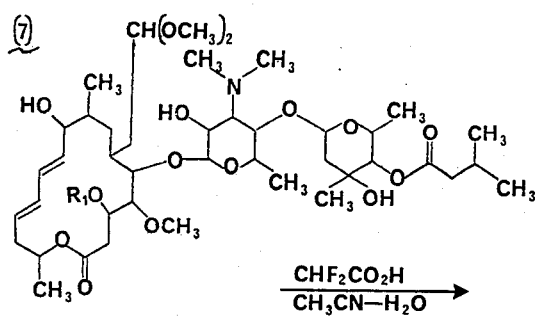

(7A) R₁ = HCO
(7B) R₁ = CH₃CO
(7C) R₁ = C₂H₅CO
(7D) R₁ = C₃H₇CO

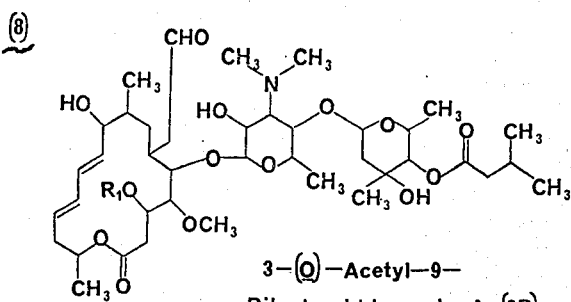

3-(O)-Acetyl-9-Dihydroniddamycin A (8B)

(8A) R₁ = HCO
(8B) R₁ = CH₃CO
(8C) R₁ = C₂H₅CO
(8D) R₁ = C₃H₇CO

The following examples further illustrate the compounds and means of preparing them according to the present invention. The number in parentheses following the chemical name identifies the compounds by such specific number, which may be alluded to in succeeding examples to identify the compounds by number. These examples, which are meant to be illustrations only, are in no way designed to limit the invention.

EXAMPLE I

Niddamycin Dimethyl Acetal (2)

The methanolic hydrochloric acid reagent employed for the preparation of (2) was prepared by mixing 22.4 ml. of concentrated HCl (37.3% HCl by weight, specific gravity at 15°/15° c. 1.189) with 3.79 liters of methanol.

A 50.00 g. (0.06378 mole) sample of niddamycin was stirred while 875 ml. of the methanolic hydrochloric acid reagent was added. The reaction mixture was stirred while final adjustment of the pH was made by addition of acid reagent in 2.0 ml. portions. It was found that when the pH reached 3.0 as measured by Hydrion Test papers (range 3.0 –5.0) dimethyl acetal formation proceeded at a convenient rate without acid catalyzed degradation of the macrolide antibiotic. After standing for 24 hours at 25° C. the reaction was complete when checked by thin layer chromatography. A solution of 4.4 g. of $K_2CO_3$ in 20 ml. of water was added while stirring to quench further acid catalyzed reaction. The reaction mixture was then concentrated in vacuo to 200 ml. and was poured into 1.0 liter of water in which 4.4 g. of $K_2CO_3$ was dissolved. The product was extracted with 1 × 200 and 2 × 100 ml. portions of chloroform. The combined chloroform extracts were washed with 3 × 100 ml. portions of water-1% $NaHCO_3$-2% $Et_3N$. The chloroform was dried over anhydrous $MgSO_4$ and was evaporated in vacuo. The residue was dissolved in 200 ml. of methanol and the methanol was evaporated in vacuo to remove residual chloroform. The residue was crystallized from methanol (170 ml.)-water (100 ml.) to give 35.3 g. of (2) after drying at 65° in a vacuum oven. The product was polymorphic undergoing a crystal change at 110° and melting at 203 - 208° C. in a sealed evacuated capillary; $[\alpha]_D^{25}$ −39.3° (C = 1.00, $C_2H_5OH$); $\lambda_{max}^{CH_3OH}$ 278 nm, $\epsilon$ = 22,750.

Analysis Calcd. for $C_{42}H_{71}NO_{15}$ (830.032): C: 60.78; H: 8.62; N: 1.69; O: 28.91

Found: C: 61.03; H: 8.70; N: 1.64; O: 29.06

EXAMPLE II

9-Dihydroniddamycin A Dimethyl Acetal (3)

A 3.00 g. (3.61 mmole) sample of niddamycin dimethyl acetal (2) was dissolved in 120 ml. of dioxane and 0.315 g. (14.45 mmole) of lithium borohydride was added. The mixture was stirred at 25° for 80 minutes and was then poured into 1.0 liter of aqueous 1% $NaHCO_3$ solution. The product was extracted with 2 × 200 and 1 × 100 ml. portions of benzene. The combined benzene layers were washed with 4 × 75 ml. of 1% aqueous $NaHCO_3$ solution, were dried over $Na_2SO_4$, and were concentrated to give 2.839 g. of crude product after drying in a vacuum oven at 65° overnight. The product was purified by chromatography on 200 g. of silica gel by elution with benzene-3% methanol to give 1.08 g. of (3) as a glass; $[\alpha]_D^{25}$ −58.5° (C = 1.00 , $C_2H_5OH$); $\lambda_{max}^{CH_3OH}$ 232 nm, $\epsilon$ = 25,900.

Analysis Calcd. for $C_{42}H_{73}NO_{15}$ (832.048): C: 60.63; H: 8.84; N: 1.68; O: 28.85

Found: C: 60.78; H: 9.09; N: 1.62; O: 28.95

EXAMPLE III

9-Dihydroniddamycin A (5)

A 0.759 g. (0.910 mmole) sample of 9-dihydroniddamycin A dimethyl acetal (3) was dissolved in 5.7 ml. of acetonitrile and a solution of 0.219 g. (2.28 mmole) of difluoroacetic acid in 5.7 ml. of water was added. The mixture was allowed to stand at 25° for 4 hours and was then diluted with 150 ml. of benzene and 50 ml. of 1% aqueous $NaHCO_3$ solution. After thorough mixing the benzene layer was separated and was washed with 2 × 25 ml. of aqueous 1% $NaHCO_3$ solution. The benzene was dried over $Na_2SO_4$ and was evaporated in vacuo to give 0.732 g. of amorphous (5) after drying at 70° for 24 hours. The product had $[\alpha]_D^{25}$ −51.3° (C = 1.00, $C_2H_5OH$); $\lambda_{max}^{CH_3OH}$ 233 nm, $\epsilon$ = 27,100.

Analysis Calcd. for $C_{40}H_{67}NO_{14}$ (785.797): C: 61.13; H: 8.59; N: 1.78; O: 28.50

Found: C: 61.02; H: 8.82; N: 1.58; O: 28.62

Thin layer chromatography on silica gel G plates with an eluent system of benzene-methanol-$NH_4OH$ (85:15:1) showed this compound to be different from authentic leucomycin $A_1$ (9-dihydroniddamycin B).

EXAMPLE IV

2′,3-Di-(O)-Acetylniddamycin Dimethyl Acetal (4B)

A 5.43 g. (6.53 mmole) sample of (2) was dissolved in 25 ml. of pyridine and 2.7 ml. of acetic anhydride was added. The mixture was allowed to stand at 25° for 21 days. Then, 4 ml. of methanol was added and 3 hours later the mixture was diluted with 200 ml. of benzene. The benzene mixture was washed with 3 × 50 ml. portions of water-1% $NaHCO_3$, was dried over $Na_2SO_4$, and was evaporated in vacuo. The residue was redissolved in benzene and was re-evaporated to remove last traces of pyridine. The residue was dried at 55° in a vacuum oven overnight to give 5.88 g. of crude (4B). The sample was crystallized from ethyl acetate-hexane to give 3.88 g. of (4B); m.p. 178° – 181°; $[\alpha]_D^{25}$ −32.7° (C = 1.00, $C_2H_5OH$); $\lambda_{max}^{CH_3OH}$ 278 nm, $\epsilon$ = 21,400.

Analysis Calcd. for $C_{46}H_{75}NO_{17}$ (914.108): C: 60.44; H: 8.27; N: 1.53; O: 29.76

Found: C: 60.26; H: 8.42; N: 1.49; O: 29.56

EXAMPLE V 3-(O)-Acetylniddamycin Dimethyl Acetal (6B)

A 3.50 g. (3.83 mmole) sample of (4B) was suspended in 150 ml. of methanol and a solution of 0.756 g. of $NaHCO_3$ in 50 ml. of water was added. The reaction mixture was stirred at 25° for 7 days (the suspension of (4B) dissolved after 4 days). The mixture was concentrated at 25° – 30° under vacuum to 90 ml. and was diluted with 300 ml. of 1% aqueous $NaHCO_3$. The product was extracted with 2 × 100 and 4 × 50 ml. portions of benzene. The combined benzene extracts were washed with 2 × 50 ml. portions of 1% aqueous $NaHCO_3$, were dried over $Na_2SO_4$, and were evaporated to give 3.20 g. of crude (6B) after drying in a vacuum oven at 65° overnight. The product was purified by crystallization from methanol-water to give 2.42 g. of (6B) with m.p. 202° –208°; $[\alpha]_D^{25}$ −10.5° (C = 1.00, $C_2H_5OH$); $\lambda_{max}^{CH_3OH}$ 278 nm, $\epsilon$ = 21,800.

Analysis Calcd. for $C_{44}H_{73}NO_{16}$ (872.079): C: 60.60; H: 8.44; N: 1.61; O: 29.35

Found: C: 60.81; H: 8.77; N: 1.56; O: 29.57

EXAMPLE VI 3-(O)-Acetyl-9-Dihydroniddamycin A Dimethyl Acetal (7B)

A 3.00 g. (3.43 mmole) sample of (6B) was dissolved in 120 ml. of dioxane at 25°. Then, 0.120 g. (5.52 mmole) of lithium borohydride was added, and the mixture was stirred at 25° for 1.5 hours. The mixture was then poured into 400 ml. of water-1% $NaHCO_3$ and the product was extracted with 2 × 100 and 2 × 75 ml. portions of benzene. The combined benzene layer was washed with 2 × 75 ml. portions of aqueous 1% $NaHCO_3$ solution, was dried over $Na_2SO_4$, and was evaporated to give 2.916 g. of crude product after drying in a vacuum oven at 65° overnight. The crude product was purified by chromatographing first on a column of 300 g. of silica gel presaturated with $NH_3$ (gas) using $CH_2Cl_2$ —$C_2H_5OH$—$CH_3CN$—$NH_3$ (liquid) (97.5: 0.75:1.5:0.2) as the eluent and then on a column of 150 g. of silica gel using benzene-methanol (98:2) as the eluent. Pure (7B) (0.900 g.) was obtained as an amorphous solid and had $[\alpha]_D^{25}$ −36.2° (C = 1.00, $C_2H_5OH$); $\lambda_{max}^{CH_3 OH}$ 232 nm, $\epsilon$ = 25,800.

Analysis Calcd. for $C_{44}H_{75}NO_{16}$ (874.086): C: 60.46; H: 8.65; N: 1.60; O: 29.29

Found: C: 60.38; H: 8.79; N: 1.44; O: 29.07

EXAMPLE VII

3-(O)-Acetyl-9-Dihydroniddamycin A (8B)

A 0.550 g. (0.630 mmole) sample of (7B) was dissolved in 4.2 ml. of acetonitrile and a solution of 0.161 g. (1.68 mmole) of difluoroacetic acid in 4.2 ml. of water was added. The mixture was allowed to stand at 25° for 5 hours and was then diluted with 100 ml. of benzene and 60 ml. of water-1% $NaHCO_3$. After thorough mixing the benzene layer was isolated and was washed with 2 × 20 ml. of aqueous 1% $NaHCO_3$ solution. The benzene layer was dried over $Na_2SO_4$ and was evaporated to give after drying at 64° overnight 0.518 g. of amorphous (8B); $[\alpha]_D^{25}$ −38.7° (C = 1.00 $C_2H_5OH$); $\lambda_{max}^{CH_3 OH}$ 2.32 nm, $\epsilon$ = 26,600.

Analysis Calcd. for $C_{42}H_{69}NO_{15}$ (828.016); C: 60.93; H: 8.40; N: 1.69; O: 28.98

Found: C: 60.76; H: 8.55; N: 1.50; O: 29.04

Thin layer chromatography on silica gel G plates with an eluent system of benzene-methanol-$NH_4OH$ (85:15:1) showed this compound to be different from authentic leucomycin $A_3$ (3-(O)-acetyl-9-dihydroniddamycin B).

The following examples and tables further illustrate the usefulness of the present compounds as active antimicrobials.

EXAMPLE VIII

Three niddamycin and two dihydroniddamycin compounds were tested for their activity against Streptococcus pyogenes C203, Diplococcus pneumoniae 6301 and Mycoplasma pneumoniae FH.

A standard two-fold tube dilution test was used. The medium and inoculum were varied with each culture.

In the test for activity against Streptococcus pyogenes C203, 5 ml. portions of brain-heart infusion broth were used with 0.1 ml. of a 1:100 dilution culture. The test was incubated for 24 hours at 37° C.

In the test for activity against Diplococcus pneumoniae 6301, 5 ml. portions of brain-heart infusion broth and 20% horse serum were used with 0.1 ml. of 1:100 dilution culture. The test was incubated for 24 hours at 37° C.

In the test for activity against Mycoplasma pneumoniae FH, 4.5 ml. portions of PPLO broth were used with 0.5 ml. of a 1:100 dilution culture. the test was incubated for 6 days at 37° C.

the compounds tested are:

2 — Niddamycin dimethyl acetal
4B — 2′,3-Di-(O)-acetylniddamycin dimethyl acetal
3 — 9-Dihydroniddamycin A dimethyl acetal
6B — 3-(O)-Acetylniddamycin dimethyl acetal
7B — 3-(O)-Acetyl-9-dihydroniddamycin A dimethyl acetal The results of the tests for the activities of the compounds are provided below in Table 1.

Table 1

| Compound | Minimum Inhibitory Concentration mcg./ml. | | |
|---|---|---|---|
| | Streptococcus pyogenes C203 | Diplococcus pneumoniae 6301 | Mycoplasma pneumoniae FH |
| 2 | 0.78 | ≤ 1.56 | 25 |
| 4B | >100 | >100 | >100 |
| 3 | 25 | >12.5 – ≤100 | 50 |
| 6B | 12.5 | >12.5 – ≤50 | 25 |
| 7B | 100 | >12.5 – ≤100 | 50 |

EXAMPLE IX

Two niddamycin derivatives were tested for their activity against 21 organisms.

An agar dilution two-fold dilution test was used for the first 14 bacterial organisms, while the remaining seven were tested by means of a two-fold tube dilution method. The incubation for all the tests was carried out at 37° C.

The samples were also tested on the standard FG (fungi) screening program.

The niddamycin base compound (M-188) was used as the control compound.

The compounds tested are:

5 — 9-Dihydroniddamycin A
8B — 3-(O)-Acetyl-9-dihydroniddamycin A

The results of the tests for the activities of the compounds are provided below in Table 2.

Table 2

| Microorganism | Minimum Inhibitory Concentration mcg./ml. | | |
|---|---|---|---|
| | Niddamycin Base | Cpd. 5 | Cpd. 8B |
| Staphylococcus aureus 9144 | 0.39 | 0.78 | 0.78 |
| Staphylococcus aureus Smith | 0.39 | 0.78 | 0.78 |
| Staphylococcus aureus Smith ER | >100 | >100 | >100 |
| Staphylococcus aureus Wise 155 | 0.78 | 1.56 | 1.56 |
| Streptococcus faecalis 10541 | 0.78 | 0.78 | 1.56 |
| Escherichia coli Juhl | >100 | >100 | >100 |
| Klebsiella pneumoniae 10031 | 12.5 | 12.5 | 25 |
| Proteus vulgaris Abbott JJ | >100 | >100 | >100 |
| Proteus mirabilis Finland No. 9 | >100 | >100 | >100 |
| Salmonella typhimurium Ed No. 9 | >100 | >100 | >100 |
| Shigella sonnei 9290 | >100 | >100 | >100 |
| Pseudomonas aeruginosa BMH No. 10 | >100 | >100 | >100 |
| Streptococcus pyogenes Roper | >100 | >100 | >100 |
| Pasteurella multocida 10544 | 12.5 | 12.5 | 12.5 |
| Mycoplasma gallispeticum S6 | 0.1 | 0.25 | 0.25 |
| Mycoplasma granularum 19168 | 1.0 | 2.5 | 5.0 |
| Mycoplasma hyorhinis 17981 | 0.25 | 0.25 | 0.5 |
| Mycoplasma pneumoniae FH | 10 | 50 | 25 |
| Crithidia fasciculata | >100 | >100 | >100 |
| Trichomonas vaginalis C1M1 | >100 | >100 | >100 |
| Haemophilus influenzae 9334 | 3.1 | 6.2 | 6.2 |

Table 2—Continued

| Microorganism | Minimum Inhibitory Concentration mcg./ml. | | |
|---|---|---|---|
| | Niddamycin Base | Cpd. 5 | Cpd. 8B |
| Fungi | | | |
| C. globosum | >100 | >100 | >100 |
| M. verrucaria | >100 | >100 | >100 |
| A. versicolor | >100 | >100 | >100 |
| P. citrinum | >100 | >100 | >100 |
| F. oxysporum | >100 | >100 | >100 |
| Alternaria label isolate | >100 | >100 | >100 |
| Rhizopus nigricans | >100 | >100 | >100 |

I claim:
1. A 9-dihydroniddamycin A compound having the structural formula:

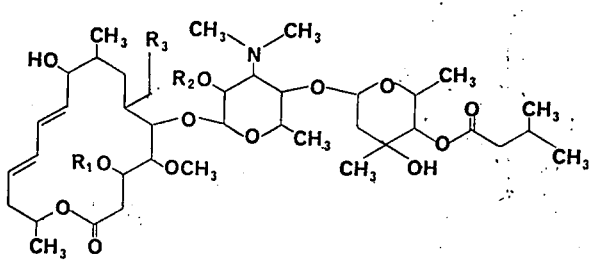

wherein $R_1$ and $R_2$ are the same or different member of the group consisting of hydrogen, HCO, $CH_3CO$, $C_2H_5CO$ or $C_3H_7CO$; and wherein $R_3$ is CHO or $CH(OCH_3)_2$.

2. A compound according to claim 1 wherein $R_1$ is hydrogen, $R_2$ is hydrogen, and $R_3$ is $CH(OCH_3)_2$.

3. A compound according to claim 2 named 9-dihydroniddamycin A dimethyl acetal.

4. A compound according to claim 1 wherein $R_1$ is hydrogen, $R_2$ is hydrogen and $R_3$ is CHO.

5. A compound according to claim 4 named 9-dihydroniddamycin A.

6. A compound according to claim 1 wherein $R_1$ is HCO, $R_2$ is hydrogen and $R_3$ is $CH(OCH_3)_2$.

7. A compound according to claim 6 named 3-(O)-formyl-9-dihydroniddamycin A dimethyl acetal.

8. A compound according to claim 1 wherein $R_1$ is HCO, $R_2$ is hydrogen and $R_3$ is CHO.

9. A compound according to claim 8 named 3-(O)-formyl-9-dihydroniddamycin A.

10. A compound according to claim 1 wherein $R_1$ is $CH_3CO$, $R_2$ is hydrogen and $R_3$ is $CH(OCH_3)_2$.

11. A compound according to Claim 10 named 3-(O)-acetyl-9-dihydroniddamycin A dimethyl acetal.

12. A compound according to claim 1 wherein $R_1$ is $CH_3CO$, $R_2$ is hydrogen and $R_3$ is CHO.

13. A compound according to claim 12 named 3-(O)-acetyl-9-dihydroniddamycin A.

14. A compound according to claim 1 wherein $R_1$ is $C_2H_5CO$, $R_2$ is hydrogen and $R_3$ is $CH(OCH_3)_2$.

15. A compound according to claim 14 named 3-(O)-propionyl-9-dihydroniddamycin A dimethyl acetal.

16. A compound according to claim 1 wherein $R_1$ is $C_2H_5CO$, $R_2$ is hydrogen and $R_3$ is CHO.

17. A compound according to claim 16 named 3-(O)-propionyl-9-dihydroniddamycin A.

18. A compound according to claim 1 wherein $R_1$ is $C_3H_7CO$, $R_2$ is hydrogen and $R_3$ is $CH(OCH_3)_2$.

19. A compound according to claim 18 named 3-(O)-butyryl-9-dihydroniddamycin A dimethyl acetal.

20. A compound according to claim 1 wherein $R_1$ is $C_3H_7CO$, $R_2$ is hydrogen and $R_3$ is CHO.

21. A compound according to claim 20 named 3-(O)-butyryl-9-dihydroniddamycin A.

22. A method of producing 9-dihydroniddamycin A consisting essentially of the steps of:
 a. reacting niddamycin with methanol to convert the niddamycin to niddamycin dimethyl acetal;
 b. reducing the niddamycin dimethyl acetal with a mixture of lithium borohydride in dioxane to 9-dihydroxyniddamycin A dimethyl acetal; and
 c. hydrolyzing said 9-dihydroxyniddamycin A dimethyl acetal with a solution of difluoroacetic acid in $CH_3CN$-$H_2O$, to provide said 9-dihydroniddamycin A.

23. A method of producing 3-(O)-acyl-9-dihydroniddamycin A consisting essentially of the steps of:
 a. acylating niddamycin dimethyl acetal with a mixture of an acyl anhydride selected from the group of anhydrides consisting of formyl, acetyl, propionyl and butyryl and pyridine to provide 2',3-di-(O)-acylniddamycin dimethyl acetal;
 b. hydrolyzing said 2',3-di-(O)-acylniddamycin dimethyl acetal with sodium bicarbonate in an aqueous solution of methyl alcohol to yield 3-(O)-acylniddamycin dimethyl acetal;
 c. reducing said 3-(O)-acylniddamycin dimethyl acetal with sodium borohydride in dioxane to provide 3-(O)-acyl-9-dihydroniddamycin A dimethyl acetal; and
 d. hydrolyzing said 3-(O)-acyl-9-dihydroniddamycin A dimethyl acetal in a mixed solvent of 50% $CH_3CN$-$H_2O$ in the presence of difluoroacetic acid to provide 3-(O)-acyl-9-dihydroniddamycin A.

24. A method of producing 3-(O)-acetyl-9-dihydroniddamycin A consisting essentially of the steps of:
 a. acetylating niddamycin dimethyl acetal with a mixture of acetic anhydride and pyridine to provide 2',3-di-(O)-acetylniddamycin dimethyl acetal;
 b. hydrolyzing said 2',3-di-(O)-acetylniddamycin dimethyl acetal with sodium bicarbonate in an aqueous solution of methyl alcohol to yield 3-(O)-acetylniddamycin dimethyl acetal;
 c. reducing said 3-(O)-acetylniddamycin dimethyl acetal with sodium borohydride in dioxane to provide 3-(O)-acetyl-9-dihydroniddamycin A dimethyl acetal; and
 d. hydrolyzing said 3-(O)-acetyl-9-dihydroniddamycin A dimethyl acetal in a mixed solvent of 50% $CH_3CN$-$H_2O$ in the presence of difluoroacetic acid to provide 3-(O)-acetyl-9-dihydroniddamycin A.

\* \* \* \* \*